United States Patent [19]

Magre et al.

[11] Patent Number: 4,932,939
[45] Date of Patent: Jun. 12, 1990

[54] SAFETY SYRINGE

[76] Inventors: George R. Magre, 2517 Via Olvera, Palos Verdes Estates, Calif. 90274; Paul Greskovics, 432 28th St., Manhattan Beach, Calif. 90266; Maria L. Magre, 2517 Via Olvera, Palos Verdes Estates, Calif. 90274

[21] Appl. No.: 319,423

[22] Filed: Mar. 6, 1989

[51] Int. Cl.⁵ ............................................. A61M 5/32
[52] U.S. Cl. ................................... 604/110; 604/195
[58] Field of Search ................ 604/195, 110, 187, 198

[56] References Cited

U.S. PATENT DOCUMENTS

| | | |
|---|---|---|
| 2,847,995 | 8/1954 | Adams . |
| 2,876,770 | 10/1955 | White . |
| 4,425,120 | 1/1984 | Sampson et al. . |
| 4,573,976 | 3/1986 | Sampson et al. . |
| 4,631,057 | 12/1986 | Mitchell . |
| 4,664,654 | 5/1987 | Strauss . |
| 4,675,005 | 6/1987 | DeLuccia ............................ 604/110 |
| 4,692,156 | 9/1987 | Haller ................................. 604/195 |
| 4,693,708 | 9/1987 | Wanderer et al. . |
| 4,695,274 | 9/1987 | Fox . |
| 4,702,738 | 10/1987 | Spencer . |
| 4,723,943 | 2/1988 | Spencer . |
| 4,725,267 | 2/1988 | Vaillancourt . |
| 4,735,618 | 4/1988 | Hagen . |
| 4,737,144 | 4/1988 | Choksi . |
| 4,747,830 | 5/1988 | Gloyer et al. ....................... 604/110 |
| 4,770,655 | 9/1988 | Haber . |
| 4,801,295 | 6/1988 | Spencer . |
| 4,808,169 | 2/1928 | Haber . |

FOREIGN PATENT DOCUMENTS 949836  6/1974  Canada .

Primary Examiner—John D. Yasko
Attorney, Agent, or Firm—Kelly Bauersfeld & Lowry

[57] ABSTRACT

An improved safety syringe is provided to prevent access to or re-use of a used medical needle. The safety syringe includes a support member for mounting a medical needle on a syringe barrel of the type having a reciprocal sliding piston carried therein. When the syringe is used, the piston is advanced to a position engaging the support member. Subsequent retraction of the piston withdraws the support member and medical needle to a safety position within the syringe barrel. In the preferred form, the needle is withdrawn through a narrow needle aperture into the syringe barrel interior, thereby substantially preventing access to the needle or re-insertion through the aperture for re-use.

11 Claims, 2 Drawing Sheets

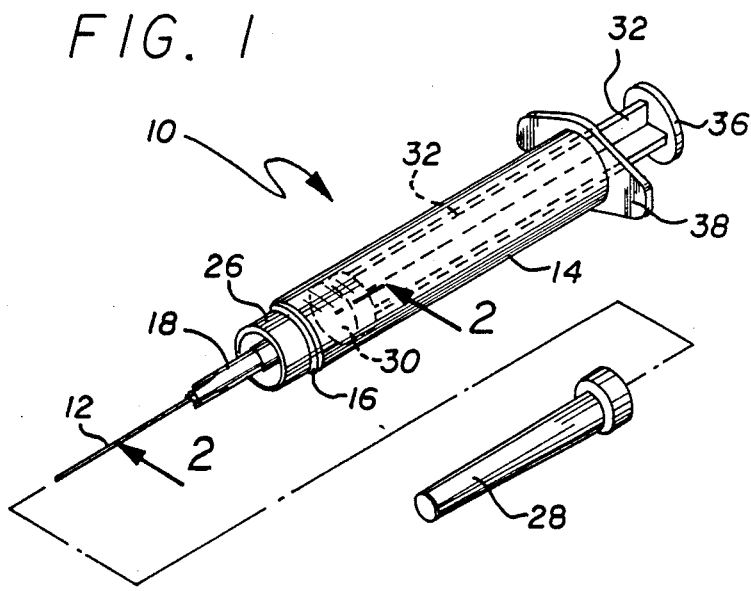
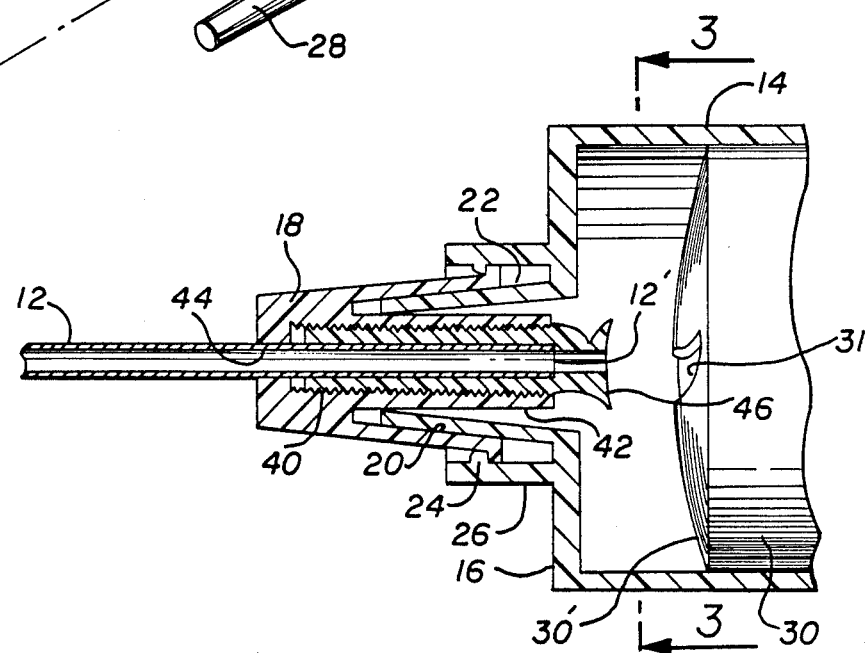
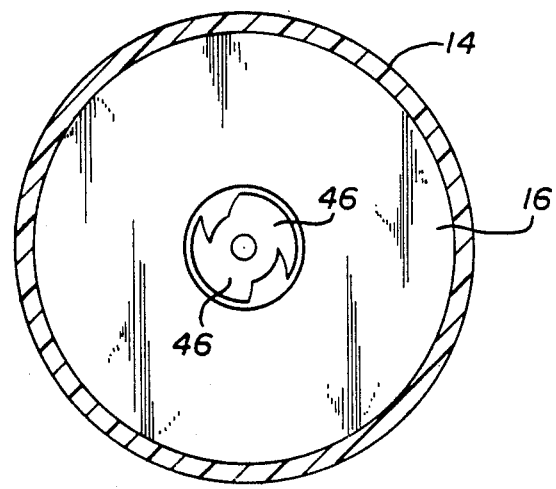

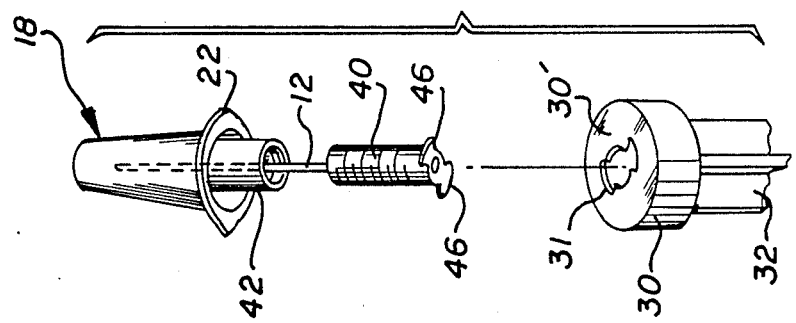
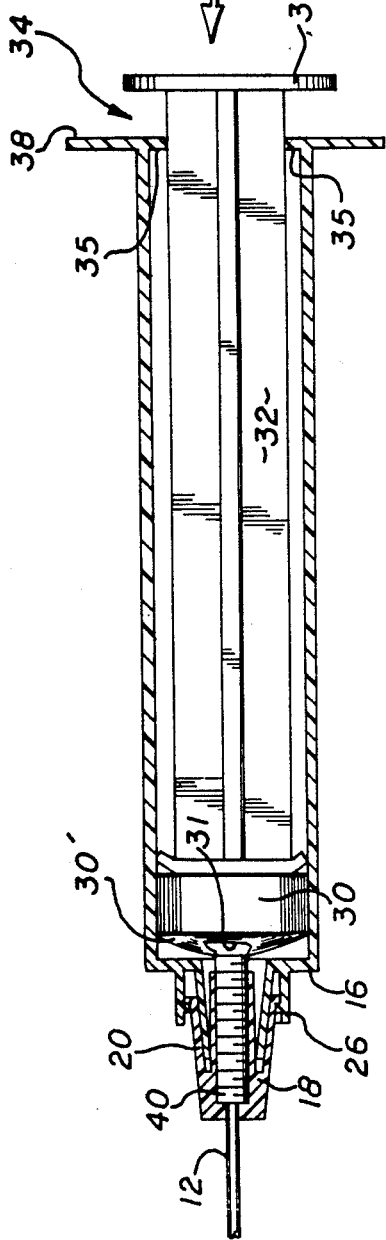
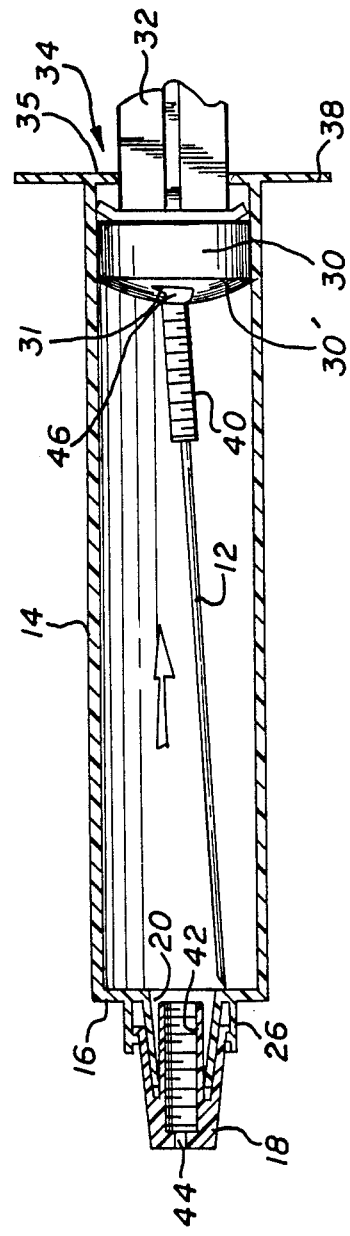

SAFETY SYRINGE

BACKGROUND OF THE INVENTION

This invention relates generally to protective devices and systems for use with medical needles to prevent accidental and/or unauthorized needle use. More particularly, this invention relates to an improved yet relatively simple syringe and needle combination designed to permit unrestricted needle use in a normal manner and subsequently to permit easy needle withdrawal to a concealed safety position protected against accidental or unauthorized re-use.

Medical needles are widely used by the health care industry in the course of patient diagnosis and/or treatment. Such medical needles are commonly used in the context of a syringe, wherein a hollow metal needle is carried by a support hub adapted for removable mounting onto the nose end of a syringe barrel. In another form, the needle is permanently affixed by a hub or the like onto the syringe barrel. In either form, the needle includes a pointed forward end adapted for transcutaneous insertion into the body of a patient for purposes drawing patient fluids for analysis or for injecting medication or other fluids into the patient. Modern medical needles are most commonly provided in a presterilized package intended for disposal after a single use, with a removable cap of plastic or the like normally covering the needle to safeguard against accidental needle sticks prior to use. After the needle is used, the cap is desirably replaced to shield the needle which is then discarded into a suitable waste receptacle.

The handling and use of medical needles requires extreme caution to prevent accidental needle stick injuries. More specifically, considerable attention and manual dexterity are required to avoid occasional infliction of needle injuries on health care workers and other unintended persons. Moreover, post-use needle sticks expose persons other than the patient to blood-borne diseases and other organisms which might be present on a used needle. For example, it is well recognized that a variety of contagious and potentially dangerous diseases such as hepatitis, acquired immune deficiency syndrome (AIDS), and others can be transmitted by contact with patient body fluids on a used medical needle.

Moreover, in recent years, discarded medical needles have been the subject of unauthorized re-use by persons involved in illegal or illicit drug abuse. Prevention of such unauthorized re-use has become extremely desirable to curb the flow and use of illegal drugs, and further to prevent uncontrolled spread of communicable diseases resulting from contact with contaminated needles.

In the past, a variety of devices have been proposed to protect medical personnel against accidental contact with medical needles, and/or to prevent unauthorized needle re-use. Many of these devices have utilized relatively complex sleeve-type structures mounted about a syringe barrel and adapted for extension or retraction to respectively cover or expose a hypodermic needle. Other needle protection mechanisms have used needle guards with narrow apertures through which the needle is manipulated for use and then withdrawn to prevent re-use. In general terms, however, these prior devices have involved relatively complex mechanical components which can interfere with normal syringe use and further result in a syringe construction of undesirably increased cost. Accordingly, prior needle protection devices and systems have generally failed to acquire any significant commercial acceptance.

There exists therefore, a significant need for further improvements in devices and systems for safeguarding against accidental or unauthorized contact with a used medical needle, particularly with respect to a relatively simple and cost efficient syringe which can be used in a normal manner followed by simple needle displacement to a shielded safety position. The present invention fulfills these needs and provides further related advantages.

SUMMARY OF THE INVENTION

In accordance with the invention, an improved safety syringe is provided for safeguarding against contact with or re-use of a used medical needle. The safety syringe includes a syringe piston for normal use in drawing fluid into or expressing fluid from a syringe barrel via a hollow medical needle. After use, the piston is adapted to withdraw the needle to a shielded safety position encased within the syringe barrel.

In a preferred form of the invention, a needle support member is designed for carrying the needle at a front or nose end of the syringe barrel, and to orient the needle in a forwardly projecting position for normal syringe use. An inboard end of the support member includes lock means for locking engagement with the syringe piston, when said piston is fully advanced within the syringe barrel. In this regard, the face of the piston is suitably formed to interlock with said lock means. Subsequent piston retraction within the syringe barrel withdraws the support member and the medical needle into the syringe barrel. In a preferred construction, the needle is withdrawn through a narrow aperture in the nose end of the barrel, thereby substantially preventing subsequent needle reinsertion through the aperture for re-access or re-use. Additional lock structure is provided to prevent withdrawal of the piston from the syringe barrel.

A preferred support member comprises a support sleeve threadably carried within a standard support hub of the type adapted for removable mounting onto the nose end of the syringe barrel. The sleeve lock means comprises at least one blade member for locking engagement with the face of the piston, such as by reception into a recess formed in the piston face, and/or by cutting engagement into a resilient piston material as the piston is advanced and rotated into contact with the blade member. Further piston rotation unthreads the support sleeve from the hub, whereupon the piston can be retracted to withdraw the sleeve and needle fully into the syringe barrel. Lateral forces acting asymmetrically between the piston and the blade member tend to displace the needle laterally within the syringe barrel, thereby misaligning the needle with a barrel aperture such that needle re-insertion through said aperture is substantially difficult or impossible.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating a safety syringe embodying the novel features of the invention;

FIG. 2 is an enlarged fragmented vertical section taken generally on the line 2—2 of FIG. 1;

FIG. 3 is a transverse vertical section taken generally on the line 3—3 of FIG. 2;

FIG. 4 is a longitudinal sectional view of the safety syringe, illustrating a syringe piston in a fully advanced position for engaging and locking with a needle support sleeve;

FIG. 5 is a longitudinal sectional view similar to FIG. 4, but illustrating withdrawal of the needle support sleeve and needle into the syringe barrel; and FIG. 6 is a fragmented exploded perspective view depicting further construction details of the safety syringe components.

DETAILED DESCRIPTION OF THE PREFERRED EMBODIMENT

As shown in the exemplary drawings, an improved safety syringe referred to generally in FIG. 1 by the reference numeral 10 is provided for preventing accidental or unauthorized reuse of a medical needle 12. The safety syringe 10 is designed for normal use in a medical environment, after which the medical needle 12 can be withdrawn quickly and easily to a protected safety position within the interior of a syringe barrel 14. Within the syringe barrel 14, the needle is substantially locked against any further access, thereby safeguarding against accidental or unauthorized human contact with a used medical needle.

The safety syringe 10 of the present invention generally comprises an assembly of standard syringe components of a type widely used in the medical industry, and appropriately modified for easy needle withdrawal to the safety position. More specifically, the safety syringe 10 includes the medical needle 12 which is normally provided as part of a presterilized needle unit adapted for rapid mounting onto the nose end 16 of the syringe barrel 14. In this regard, medical needle 12 is normally carried by a support hub 18 of molded plastic or the like and having a rearwardly expanding conical shape adapted to fit snugly over a generally conical nose cone 20 (FIG. 2) on the nose end 16 of the syringe barrel. The support hub 18 includes an outwardly projecting rear rim 22 for threaded engagement with a spiral thread 24 formed on the inner diameter surface of a nose cylinder 26 disposed about the nose cone 20. When the support hub 18 is seated on the nose cone 20 of the syringe barrel 14, the hollow medical needle 12 has an inboard end 12' exposed to the interior of the syringe barrel 14. As known in the art, the support hub 18 and medical needle 12 are normally provided in a presterilized package with a protective cover cap 28 for rapid mounting onto the syringe barrel 14, as described above, after which the cap 28 is easily removed to expose the needle 12 for use.

The syringe barrel 14 is also normally provided as a separate presterilized package for assembly with the needle unit at the time of use. The syringe barrel 14 is adapted for sliding reception of a generally cylindrical syringe piston 30 which is conventionally carried at the forward end of an elongated piston rod 32. The piston rod 32 is shown with an x-shaped cross section for self-guided displacement within the syringe barrel. The piston rod extends in the aft direction through an open rear end 34 (FIGS. 4 and 5) to the exterior of the syringe barrel, with one or more ribs 35 conveniently permitting one-way insertion of the piston into the syringe barrel. An enlarged thumb disk 36 is normally mounted on the rearward end of the piston rod 32 and is easily manipulated in cooperation with finger flanges 38 on the syringe barrel to advance or retract the piston 30. Retraction motion in a rearward direction is effective to draw fluid such as medication through the hollow needle 12 into the interior of the syringe barrel 14. Alternately, advancing piston motion functions to expel or express fluid from the barrel interior through the needle 12, with the needle 12 providing a transcutaneous conduit in communication with the body of a patient. Alternately, the needle and syringe components may be provided in other configurations, such as mounting the needle directly and fixedly onto the nose end of the syringe barrel to provide a pre-assembled syringe product.

In accordance with a primary aspect of the invention, the medical needle 12 is removably carried by the support hub 18 to permit separation of the needle from the support hub after a single use of the safety syringe. More specifically, the syringe piston 30 is designed to engage and lock with structure carrying the medical needle for purposes of withdrawing the medical needle fully into the interior of the syringe barrel to a safeguarded or safety position substantially protected against further human contact.

As shown in the illustrative drawings (FIGS. 2 and 4–6), the rearward end of the medical needle 12 is secured within a support member in the form of a generally cylindrical support sleeve 40. A preferred support sleeve geometry includes external threads designed for rotational thread-in connection within an internally threaded inner sleeve 42 formed integrally with the support hub 18. This inner sleeve 42 is sized and shaped to fit rearwardly into the nose cone 20 of the syringe barrel 14. When the hub 18 is mounted on the syringe barrel. The inner sleeve 42 includes sufficient internal threading or other surface discontinuities to accommodate thread-in attachment of the support sleeve 40. Importantly, as viewed best in FIGS. 2, 4 and 5, the inner sleeve 42 of the support hub 18 is positioned rearwardly with respect to a narrow forward aperture 44 through which the needle 12 slidably extends with relatively close tolerance.

The aft end of the support sleeve 40 includes lock means 46 for locking engagement with the syringe piston 30, when said piston is advanced to a fully forward position within the syringe barrel. As shown in the exemplary drawings, the lock means 46 comprises one or more blade members having arcuate and/or relatively sharp edges for engaging the face 30' of the syringe piston 30. In this regard, for facilitated engagement with the blade members 46, the piston face 30' is formed from a sufficiently resilient plastic material for cut-in engagement with the blade members. A forwardly presented recess 31 is also desirably provided in the piston face 30' to enhance and facilitate blade member engagement.

When the piston 30 is advanced to a fully forward position within the syringe barrel 14, subsequent to syringe use, the thumb disk 36 is appropriately rotated as depicted FIG. 4 while pressing the piston face 30, against the blade members 46 of the support sleeve 40. During such rotation, the blade members 46 seat within the piston recess 31 and further cut into the resilient piston face for secure locking engagement therewith.

Further rotation of the thumb disk 36 rotates the support sleeve 40 and medical needle 12 within the support hub 18 about an axis generally coaxial with the needle and the piston rod. Sufficient rotation of the components unthreads the support sleeve from the hub. In this regard, the directional threading of the components is chosen for support sleeve rotation in a direction which does not loosen the support hub 18 with respect to the nose cylinder 26.

When the support sleeve 40 is separated from the support hub 18, the syringe piston 30 can be retracted fully within the syringe barrel 14. During such retraction motion, the piston 30 carries the support sleeve 40 and medical needle 12 in a rearward direction toward a position fully within the syringe barrel 14, as view in FIG. 5. The medical needle 12 is withdrawn through the narrow support hub aperture 44 and further beyond the inner sleeve 42 of the hub 18 and further to a position with the pointed end of the needle disposed inboard with respect to the nose end 16 of the syringe barrel 14. The resilient nature of the piston face 30, beneficially results in nonuniform laterally directed forces or stresses which cause the needle 12 to shift laterally as soon as it clears the support hub 18. Such lateral shifting displaces the needle point to a position where reinsertion through the support hub 18 is substantially precluded. In this regard, the rib 35 at the aft end 34 of the syringe barrel 14 prevents rearward piston removal from the syringe barrel 14. Alternatively, other types of lock structure can be used to prevent piston withdrawal from the barrel.

Accordingly, the safety syringe 10 of the present invention can be used in a normal manner for drawing or injecting medical fluids. Bulky sleeve-type safety shields or other significant protective components are not present. However, after a single use, the needle 12 can be engaged and withdrawn into the barrel interior, wherein such displacement arises entirely from manipulation at the rear end of the syringe barrel. There is no need to replace the protective cover cap 28 as the needle is withdraw quickly and easily to a permanently safeguarded position within the syringe barrel. The barrel 14 with encased needle 12 can then be safely disposed in a suitable receptacle.

A variety of modifications and improvements to the safety syringe of the present invention will be apparent to those skilled in the art. Accordingly, no limitation on the invention is intended by way of the foregoing description and accompanying drawings, except as set forth in the appended claims.

What is claimed is:

1. A safety syringe, comprising:
   a medical needle unit including a needle and a support member carrying said needle;
   a syringe barrel having a nose end;
   means for removably mounting said support member and needle at said nose end of the syringe barrel; and
   a syringe piston slidably reciprocal within said syringe barrel, said piston and said medical needle unit including lock means interengageable upon movement of said piston to a fully advanced position within said syringe barrel, whereupon said piston is retractable within said barrel to withdraw said medical needle unit to a position substantially encased within said barrel, said lock means including at least one blade member formed on said support member for engagement with said piston, and said piston including a piston face of resilient material for cutting engagement by said blade member.

2. The safety syringe of claim 1 wherein said piston face defines a recess for at least partial reception of said blade member.

3. The safety syringe of claim 1 wherein said piston includes a piston face having a recess formed therein, said blade member being at least partially receivable onto said recess.

4. The safety syringe of claim 1 wherein said medical needle unit comprises a needle, a support sleeve carrying said needle, and a support hub removably carrying said support sleeve, said mounting means being formed cooperatively on said support hub and said nose end of the syringe barrel for removably mounting said support hub onto the syringe barrel, said lock means being cooperatively formed on said piston and said support sleeve for interengagement therebetween, whereupon said support sleeve and said needle are withdrawable together to said safety position.

5. The safety syringe of claim wherein said support sleeve is threadably carried by said support hub.

6. The safety syringe of claim 5 wherein said mounting means includes means for threadably mounting said support hub onto the syringe barrel.

7. The safety syringe of claim 5 wherein said support hub includes an inner sleeve for threadably carrying said support sleeve, said needle projecting from said support sleeve through a narrow aperture formed in said support hub.

8. The safety syringe of claim 1 wherein said syringe barrel includes means for preventing retraction of said piston from said barrel.

9. A safety syringe, comprising:
   a medical needle unit including a needle, a support member carrying said needle, and a support hub removably carrying said support member; and
   a syringe unit including a syringe barrel, a piston slidably reciprocal within said barrel, and means for preventing removal of said piston from said barrel;
   said syringe barrel having a nose end with means for removably mounting said support hub in a position with said needle communicating with the interior of said barrel;
   said piston and said support member including lock means interengageable upon movement of said piston to a fully advanced position within said barrel, whereupon said piston is retractable to withdraw said support member and said needle to a safety position substantially concealed within said barrel, said lock means including at least one blade member on said support member, and said support member including a support sleeve threadably carried by said support hub, said piston being rotatable subsequent to engagement with said blade member to separate said support sleeve from said support hub followed by retraction of said piston to displace said needle to the safety position.

10. The safety syringe of claim 9 wherein said piston includes a piston face of resilient material for cutting engagement by said blade member.

11. The safety syringe of claim 9 wherein said piston face defines a recess for at least partial reception of said blade member.

* * * * *